United States Patent [19]

Toikka

[11] Patent Number: 5,233,034
[45] Date of Patent: Aug. 3, 1993

[54] PROCESS FOR THE PURIFICATION OF HEMIN, A NOVEL DERIVATIVE AND PROCESS FOR ITS PREPARATION

[75] Inventor: Jarmo Toikka, Turku, Finland
[73] Assignee: Huhtamaki Oy, Turku, Finland
[21] Appl. No.: 773,873
[22] PCT Filed: Apr. 9, 1990
[86] PCT No.: PCT/FI90/00097
 § 371 Date: Oct. 17, 1991
 § 102(e) Date: Oct. 17, 1991
[87] PCT Pub. No.: WO90/12801
 PCT Pub. Date: Nov. 1, 1990

[30] Foreign Application Priority Data

Apr. 26, 1989 [FI] Finland .................................. 891988

[51] Int. Cl.⁵ .......................................... C07D 487/22
[52] U.S. Cl. ...................................................... 540/145
[58] Field of Search ......................................... 540/145
[56] References Cited

U.S. PATENT DOCUMENTS 4,761,472 8/1988 Schultze ............................... 540/145

OTHER PUBLICATIONS

Labbe et al., "A New Method of Hemin Isolation," Biochem., Biophys. Acta 1957, 26, 437.
Merck Index, 4534 Hemin, p. 4537.
"Organic Syntheses", Coll. vol. 3, pp. 442–443 (1955) by John Wiley and Sons, Inc.
"Modern Experimental Organic Chemistry" by Fishel and Fort, pp. 23–35 (1971), by the Macmillan Company.

Primary Examiner—Thurman K. Page
Assistant Examiner—Jyothsna Venkat
Attorney, Agent, or Firm—Wolf, Greenfield & Sacks

[57] ABSTRACT

Process for the purification of hemin by dissolving raw hemin into 1,3-dimethyl-2-imidazolidinone (DMI), the mixture is allowed to cool in order to crystallize the hemin in the form of a 1:3-adduct of hemin and DMI, whereafter the adduct obtained is split by mixing the same with warm water, a lower alcohol or in a mixture thereof, or by heating in a vacuum, and the liberated hemin is recovered. The invention also concerns a novel hemin derivative, that is the 1:3-adduct of hemin and DMI, and a process for its preparation.

13 Claims, No Drawings

PROCESS FOR THE PURIFICATION OF HEMIN, A NOVEL DERIVATIVE AND PROCESS FOR ITS PREPARATION

BACKGROUND OF THE INVENTION

This invention concerns a new process for the purification of hemin, a novel hemin derivative usable in the process, as well as a process for its preparation.

Hemin is used in medicine i.e., as a water soluble complex compound with basic amino acids, for example L-arginine, for the preparation of pharmaceutical preparations, especially injection preparations, which may be used for the treatment of various types of anemia and especially for the treatment of porphyrism, (see FI-patent 68970).

Hemin may be prepared by splitting hemoglobin from blood using different methods. Thus as the starting material, for example, whole blood or red cell concentrates may be used. According to a modification of a method described by Labbe et al. in the publication Biochem., Biophys. Acta 1957, 26, 437, hemin may be isolated from human blood (red cell concentrate) with a mixture of acetone and acetic acid. In this treatment the cell material and the proteins are separated as a solid substance, which is removed by centrifugation. The centrifuged solution contains the hemin. By evaporating the major part of the solvents the hemin is made to crystallize at room temperature.

A problem has, however, been the preparation of hemin in a form sufficiently pure for medicinal use. According to literature (Fischer, Hans: Organic Synthesis, Collective, Vol. 442-443 (1955) hemin may be crystallized from chloroform pyridine glacial acetic acid. Crystallization from chloroform pyridine-glacial acetic acid does not purify hemin very effectively. In the DE-publication 36 08 091 A1 is disclosed a process for the separation and purification of hemin by crystallizing the same from an acid aqueous solution in the presence of tensides. A disadvantage of this purification process is the insufficient degree of purity of the hemin obtained, which is approximately 98% by weight.

SUMMARY OF THE INVENTION

Now it has, according to the invention, been discovered that hemin may be prepared in a form sufficiently pure for its medical use. Thus the invention concerns a novel process for the purification of hemin which makes it possible to prepare hemin with a good yield and in a very pure form, typically with a degree f purity of 99 to 100%. The invention concerns also a novel hemin derivative formed in the process, as well as a process for its preparation.

DETAILED DESCRIPTION

Thus the invention concerns a novel process according to which raw hemin prepared for example as described above, is dissolved while heating in 1,3-dimethyl-2-imidazolidinone (DMI), the mixture is allowed to cool in order to crystallize the hemin as a 1:3 adduct of hemin and DMI, whereafter the adduct obtained is split by treating the same in warm water, a lower alcohol, or in a mixture thereof, or by heating in a vacuum, and the liberated hemin is recovered.

The invention concerns also as a novel compound the adduct of hemin and DMI which may be illustrated with the following formula

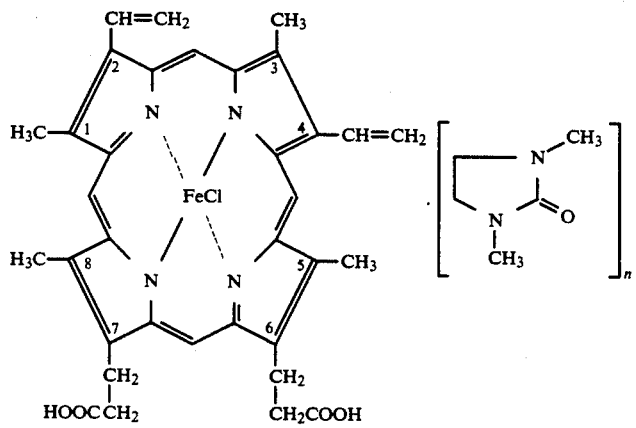

In the formula, $n=3$ when the adduct is washed and dried in a vacuum at a temperature not higher than 50° C. By drying in a vacuum at higher temperatures, DMI is split off from the adduct, whereby n will vary between 0 and 3. The composition of the adduct may be determined with HPLC. The adduct is a crystalline product which is completely resolved at 105° C.

The process according to the invention is preferably carried out by using DMI in an amount by weight which is approximately 5 to 10 times, especially approximately 6 to 8 times in excess with respect to the weight of hemin. Hemin dissolves very well in hot DMI. This the dissolution of hemin preferably takes place at a temperature of approximately 60° to 80° C. The adduct formed after dissolving while hot crystallizes when the solution is cooled to a temperature below room temperature but above approximately 8° C. (the melting point of DMI is 8° C.), preferably it is cooled to about 10° C., whereby the hemin-DMI adduct is crystallized with a small crystallization loss and in a very pure form. The adduct may be recovered and stored for its later use.

For the preparation of hemin, the adduct is resolved by mixing it with warm water, a lower alcohol, or a mixture thereof. As a lower alcohol, preferably a $C_1$-$C_4$ alcohol is used. For aseptical reasons a 70% ethanol solution is highly preferred. Alcohol is used in an excess with respect to the hemin, preferably at least in an amount by weight which is at least 4 times, advantageously about 6 times the weight of hemin. During the resolution, the mixture is heated, preferably at least to about 50° C., for example to 60 to 70° C.

The following example illustrates the invention.

EXAMPLE

According to the above mentioned process modification of Labbe et al., hemin is isolated from a red cell concentrate with a mixture of acetone and acetic acid. Thus the cell material and the proteins precipitate, the mixture is centrifuged and the supernatant containing the hemin is recovered. The major part of the acetone and the acetic acid is evaporated and the residue is allowed to cool to room temperature overnight. The hemin crystallizes and it is filtered and washed. Finally the hemin is dried in a vacuum.

The hemin thus obtained is dissolved in an 8-fold amount of DMI by heating the mixture to 70° C. The mixture is filtered while hot and it is allowed to cool to 10° C., at which temperature it is stirred for an additional hour. The hemin crystallizes from the solution in the form of a pure DMI-adduct, which is filtered and washed with a small amount of ethanol, and dried. The composition of the adduct is, according to HPLC-analysis, 1:3 hemin:DMI, when the drying is effected at approximately 50° C. At higher temperatures the amount of DMI is smaller due to its splitting off. From the rodlike black adduct crystals DMI is split off completely already at 105° C.

The adduct is resolved by mixing the same for one hour at 60° C. in 70% ethanol, of which a 6-fold amount of weight is used compared to hemin. After mixing the product is filtered and washed with small amount of absolute ethanol, whereby small residual amounts of water are removed. Finally the hemin is dried in a vacuum. The purity of the end product is 99 to 100% of hemin.

I claim:

1. A process for the purification of hemin, comprising the steps of:
    dissolving raw hemin in 1,3-dimethyl-2-imidazolidinone (DMI) while heating to form a mixture thereof;
    allowing the mixture to cool in order to crystallize a 1:3-adduct of hemin and DMI; and
    treating the adduct by splitting the same and recovering the liberated hemin.

2. The process of claim 1, wherein the raw hemin is dissolved in an amount by weight of DMI which is 5 to 10 times the weight of hemin.

3. The process of claim 2, wherein the raw hemin is dissolved in an amount by weight of DMI which is 8 to 10 times the weight of hemin.

4. The process of claim 1, wherein the mixture of hemin and DMI is allowed to cool to a temperature between 8° C. and room temperature in order to crystallize the hemin-DMI adduct.

5. The process of claim 4, wherein the adduct of hemin and DMI is crystallized at a temperature of about 10° C.

6. The process of claim 1, wherein the adduct is treated in warm water, a lower alcohol, or a mixture thereof.

7. The process of claim 6, wherein the adduct is treated in an aqueous lower alcohol.

8. The process of claim 7, wherein the aqueous lower alcohol solution is 70% ethanol.

9. The process of claim 7, wherein the adduct is treated by heating to a temperature above 50° C.

10. The process of claim 1, wherein the adduct is treated at a temperature of 60° to 70° C.

11. The process of claim 1, wherein the adduct is treated by heating in a vacuum.

12. The process of claim 11, wherein the adduct is treated by heating in the vacuum at 105° C.

13. A process for the preparation of a 1:3-adduct of hemin and 1,3-dimethyl-2-imidazolidinone (DMI) comprisng the steps of:
    dissolving raw hemin in DMI while heating to obtain a mixture thereof;
    allowing the mixture to cool in order to crystallize a 1:3-adduct of hemin and DMI; and
    recovering and drying the adduct at a temperature not higher than 50° C.

* * * * *

UNITED STATES PATENT AND TRADEMARK OFFICE
CERTIFICATE OF CORRECTION

PATENT NO. : 5,233,034
DATED      : August 3, 1993
INVENTOR(S): Toikka

It is certified that error appears in the above-indentified patent and that said Letters Patent is hereby corrected as shown below:

Column 2, line 1, delete "f" and substitute --of--.

Signed and Sealed this

Twenty-second Day of March, 1994

Attest:

BRUCE LEHMAN

Attesting Officer                 Commissioner of Patents and Trademarks